United States Patent

Knoth, Jr. et al.

[11] 3,975,447
[45] Aug. 17, 1976

[54] PREPARATION OF AROMATIC PHOSPHINE OXIDES BY REACTION OF DIARYLHALOPHOSPHINE AND BENZYLIC HALIDE

[75] Inventors: Walter Henry Knoth, Jr., Mendenhall, Pa.; Joseph John Mrowca, Wilmington, Del.

[73] Assignee: E. I. Du Pont de Nemours and Company, Wilmington, Del.

[22] Filed: Oct. 3, 1974

[21] Appl. No.: 511,531

[52] U.S. Cl. ............................................. 260/606.5 P
[51] Int. Cl.² ............................................. C07F 9/02
[58] Field of Search ............................. 260/606.5 P

[56] References Cited
UNITED STATES PATENTS

| | | | |
|---|---|---|---|
| 3,325,546 | 6/1967 | Hays | 260/606.5 P |
| 3,746,758 | 7/1973 | Spivak | 260/606.5 P |

OTHER PUBLICATIONS

Dörken, Chem. Ber., vol. 21, pp. 1505–1515 (1888).
Rauhut et al., J. Org. Chem., vol. 26, 4628–4632 (1961).
Michaelis, Ber. vol. 18, 2117 (1885).
Chemical Reviews, vol. 60, 247–248 (1960).
J.A.C.S. vol. 81, pp. 3805–3807 (1959).

*Primary Examiner*—Helen M. S. Sneed

[57] ABSTRACT

Phosphine oxides of the formula

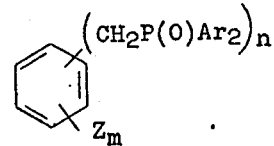

wherein Ar is a mono- or di-carbocyclic aromatic radical which may be substituted by up to 5 substituents selected from the group consisting of halogen and alkyl of 1 to 3 carbon atoms, Z is halogen or alkyl of 1 to 3 carbon atoms, $n$ is a whole number from 1 to 3, $m$ is a whole number from 0 to 5, and $n + m$ is a whole number from 1 to 6, are prepared by reacting 1. a benzylic halide of the formula

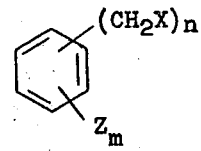

wherein X is chlorine, bromine or iodine; and Z, $n$ and $m$ are as specified above, 2. a diarylhalophosphine of the formula $Ar_2PX'$ wherein Ar is as specified above, and X' is chlorine, bromine or iodine, and 3. an alkali metal hydroxide or an alkaline earth metal hydroxide.

7 Claims, No Drawings

PREPARATION OF AROMATIC PHOSPHINE OXIDES BY REACTION OF DIARYLHALOPHOSPHINE AND BENZYLIC HALIDE

BACKGROUND OF THE INVENTION

1. Field of the Invention

This invention relates to a new process for preparing aromatic phosphine oxides which are useful as flame retardants for organic polymers.

2. Description of the Prior Art

Dörken, in Chem. Berichte (1888), 21, p. 1505–1515, teaches the preparation of aromatic phosphine oxides by a two-step process starting with diarylhalophosphine. Chlorodiphenylphosphine is reacted with benzyl chloride to yield benzyldiphenylphosphine dichloride in accordance with the following equation in which the symbol Ph is used to represent the phenyl radical:

When this dichloride is hydrolyzed in water, benzylphenylphosphine oxide is obtained.

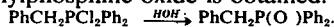

Horner et at., in Chem. Berichte (1962), 95, p. 581–601, teach the two-step reaction:

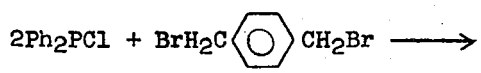

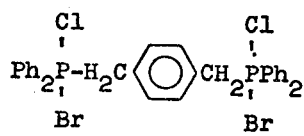

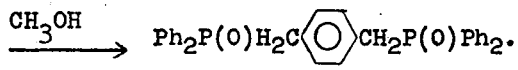

Somewhat related phosphine oxides have been prepared in a one-step process starting with an aliphatic phosphine oxide rather than a diarylhalophosphine. Rauhut et al., Jour. Org. Chem., vol. 26, p. 4628–4632 (1961), teach the reaction of bis(2-cyanoethyl) phosphine oxide with 2,4-dichlorobenzyl chloride in methanolic sodium hydroxide to give bis(2-cyanoethyl) (2,4-dichlorobenzyl)phosphine oxide.

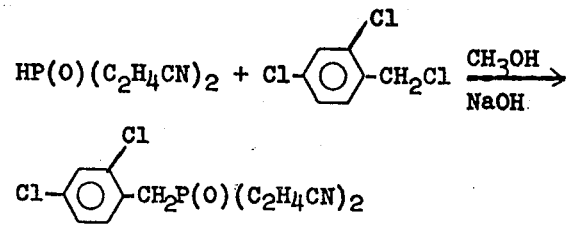

SUMMARY OF THE INVENTION

In accordance with this invention a one-step process for preparing aromatic phosphine oxides of the formula

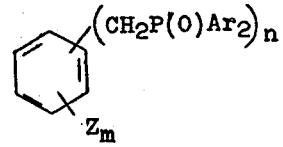

wherein AR is a mono- or di-carbocyclic aromatic radical which may be substituted by up to 5 substituents selected from the group consisting of halogen and alkyls to 1 to 3 carbon atoms, Z is halogen or alkyl of 1 to 3 carbon atoms, $n$ is a whole number from 1 to 3, $m$ is a whole number from 0 to 5, and $n + m$ is a whole number from 1 to 6 has been discovered which comprises reacting 1. a benzylic halide of the formula

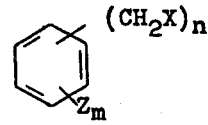

wherein X is chlorine, bromine or iodine; and Z, $n$ and $m$ are as specified above, 2. a diarylhalophosphine of the formula

wherein Ar is as specified above, and X' is chlorine, bromine or iodine, and 3. a hydroxide selected from the group consisting of alkali metal hydroxides and alkaline earth metal hydroxides. Yields of the order of 50 to 100% are obtained in short reaction times.

DETAILED DESCRIPTION OF THE INVENTION

The reaction of this invention is illustrated by the equation:

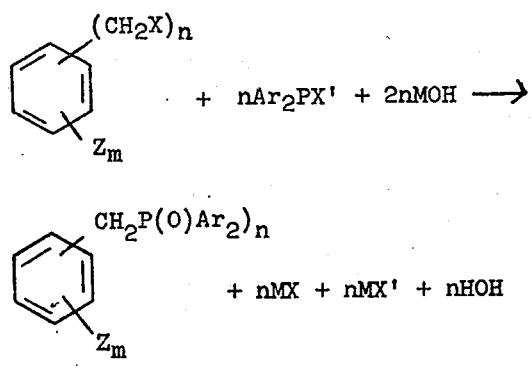

in which M is an alkali metal or an alkaline earth metal and Ar, Z, X, X', $n$ and $m$ are as defined above.

Suitable benzylic halides for use in accordance with this invention include p-xylylene dichloride, 0-xylylene dichloride, 2,4,6-tris(chloromethyl)mesitylene, benzyl chloride, benzyl bromide, p-bromobenzyl bromide, m-xylylene dibromide, p-methylbenzyl chloride, benzyl iodide, p-xylylene diiodide, p-ethylbenzyl chloride, p-n-propylbenzyl chloride, p-chlorobenzyl chloride, p-iodobenzyl chloride, p-fluorobenzyl chloride, α,2,4,5-tetrachlorotoluene, α,2,6-trichlorotoluene, α,3,4-trichlorotoluene, 3,4-dimethylbenzyl chloride, 2,5-dimethylbenzyl chloride, and tert.-pentylbenzyl chloride.

Suitable diarylhalophosphines for use in accordance with this invention include diphenylchlorophosphine, bis(p-methylphenyl)chlorophosphine, diphenyliodophosphine, phenylpentafluorophenylbromophosphine, bis(p-chlorphenyl)bromophosphine, diphenylbromophosphine, bis(p-ethylphenyl)chlorophosphine, bis(p-n-propylphenyl)chlorophosphine, bis(p-bromophenyl)chlorophosphine, bis(m-bromophenyl)chlorophosphine, bis(2,4,5-trimethylphenyl)chlorophosphine, and bis(1-naphthyl)chlorophosphine.

Specific combinations of benzylic halide and diarylhalophosphine and the resulting phosphine oxide product can be found in Table I.

TABLE I

| Benzylic Halide | Diarylhalophosphine | Phosphine Oxide Product |
|---|---|---|
| $PhCH_2Cl$ | $Ph_2PCl$ | $Ph_2P(O)CH_2Ph$ |
| $p\text{-}BrC_6H_4CH_2Br$ | $[p\text{-}CH_3C_6H_4]_2PCl$ | $[p\text{-}CH_3C_6H_4]_2P(O)CH_2C_6H_4Br$ |
| $m\text{-}C_6H_4(CH_2Br)_2$ | $Ph_2PI$ | $m\text{-}C_6H_4[CH_2P(O)Ph_2]_2$ |
| $p\text{-}CH_3C_6H_4CH_2Cl$ | $Ph(C_6F_5)PCl$ | $Ph(C_6F_5)P(O)CH_2C_6H_4CH_3$ |
| $PhCH_2I$ | $[p\text{-}ClC_6H_4]_2PCl$ | $[p\text{-}ClC_6H_4]_2P(O)CH_2Ph$ |
| $2,3,5\text{-}Cl_3C_6H_2CH_2Cl$ | $(p\text{-}BrC_6H_4)_2PCl$ | $(p\text{-}BrC_6H_4)_2P(O)CH_2C_6H_2Cl_3$ |
| $3,4\text{-}(CH_3)_2C_6H_3CH_2Cl$ | $[2,4,5\text{-}(CH_3)_3C_6H_2]_2PCl$ | $[2,4,5\text{-}(CH_3)_3C_6H_2]_2P(O)CH_2C_6H_3(CH_3)_2$ |
| $2,6\text{-}Cl_2C_6H_3CH_2Cl$ | $(1\text{-}C_{10}H_7)_2PCl$ | $(1\text{-}C_{10}H_7)_2P(O)CH_2C_6H_3Cl_2$ |

The hydroxide used in accordance with this invention may be an alkali metal or an alkaline earth metal hydroxide. Suitable alkali metal hydroxides include sodium, lithium and potassium hydroxides. Suitable alkaline earth metal hydroxides include magnesium, calcium and barium hydroxides.

The reaction of this invention is preferably carried out in the presence of water and/or an organic solvent. The preferred solvents are those which are capable of dissolving at least about 1% by weight of water. Suitable solvents include ethers, such as dimethyl ether, diethyl ether, dimethoxyethane and tetrahydrofuran; nitriles such as acetonitrile, propionitrile and benzonitrile; tertiary amides such as dimethylformamide, dimethylacetamide and diethylacetamide; alcohols such as methanol, ethanol and butanol; sulfones such as tetramethylene sulfone, ethyl benzyl sulfone, diphenyl sulfone and dibenzyl sulfone; sulfoxides such as dimethyl sulfoxide, tetramethylene sulfoxide, diphenyl sulfoxide and dibenzyl sulfoxide; and aromatics such as benzene, o-dichlorobenzene and pyridine.

The ratio in which the three specified reactants are brought together to carry out the process of this invention is not critical. Any amounts brought together will produce at least some of the phosphine oxide product. For practical rates or reaction it is preferred that the diarylhalophosphine and/or the hydroxide be present in modest excess over the equivalent amounts required in the above equation.

The temperature at which the reaction of this invention is carried out may be varied over a wide range, e.g., from about −50° to about 250°C. and above. It is preferred to operate in the range from about 20° to 150°C. External heating is not required to initiate the reaction and the reaction is mildly exothemic. The use of external heating above that supplied by the reaction is sometimes desirable to increase the crystallinity of the product phosphine oxide. A convenient way to accomplish this is to employ a solvent boiling in the range from about 60° to 150°C. and to run the reaction at the reflux temperature of the solvent.

When the reactants are brought together, at least some of the desired product is formed almost immediately. However, the yield increases with time. Reaction times from about 1 minute to about 4 hours are preferred.

Pressure is not a critical variable in this reaction. Both subatmospheric and superatmosperic pressures may be employed. Atmospheric pressure is preferred for convenience.

In a preferred embodiment of this invention the diarylhalophosphine and benzylic halide are combined in the organic solvent and a concentrated aqueous solution of the alkali metal hydroxide is added. Alternatively, water may be omitted and the alkali metal hydroxide added neat or as a solution in the same or a different organic solvent. Methanol is preferred as the solvent for this latter procedure. The reaction begins immediately and stirring and heating are applied.

In many of the variations of the process the product phosphine oxide precipitates from the reaction mixture and is isolated by filtration. It may be washed with water and/or another solvent until it is free of hydroxide and halide ions. It may be further purified by recrystallization. If the phosphine oxide does not precipitate from the reaction mixture, it may be recovered by conventional means such as solvent removal, solvent extraction or precipitation by addition of a nonsolvent.

EXAMPLES OF THE INVENTION

The following examples are given to illustrate the invention. All percentages are by weight.

EXAMPLE 1

A mixture of 16 g of chlorodiphenylphosphine, 6 g of p-xylylenedichloride and 100 ml of 1,2-dimethoxyethane was refluxed for 4 hours in a nitrogen atmosphere and cooled to ambient temperature. Two ml. of water was added and the solution was stirred for 5 minutes. No effect was observed. An aliquot of the solution was removed and further diluted with water, precipitating p-xylylenedichloride thus demonstrating that no reaction had yet occured. The addition of aqueous sodium hydroxide to a second portion of the reaction mixture without heating caused the rapid precipitation of $p\text{-}C_6H_4[CH_2P(O)Ph_2]_2$, identified by infrared analysis.

EXAMPLE 2

A solution of 1.5 g. of sodium hydroxide in 15 ml. of water was added to a solution of 4 g. of chlorodiphenylphosphine and 1.5 g. of p-xylylenedichloride in 25 25 ml. of 1,2-dimethoxyethane. The mixture became warm and crystalline $p\text{-}C_6H_4[CH_2P(0)Ph_2]_2$ began separating within 1 minute.

EXAMPLE 3

A solution of 6.4 g. of sodium hydroxide in 20 ml. of water was added to a solution of 16.0 g. of chlorodiphenylphosphine and 6.0 g. of p-xylylenedichloride in 100 ml. of tetrahydrofuran. The mixture was stirred for 30 minutes during which time the heat of reaction maintained a temperature of about 55°C. Filtration gave 11 g. (63%) of p-$C_6H_4[CH_2P(O)Ph_2]_2$ which was washed thoroughly with water and methanol before drying.

EXAMPLES 4 – 9

Examples 4–9 were conducted in the manner of Example 3 with the modifications stated in Table II.

TABLE II

| Example No. | p-$C_6H_4(CH_2Cl)_2$ (g) | $Ph_2PCl$ (g) | Solvent (ml) | NaOH (g) | $H_2O$ (ml) | Reaction Conditions | Yield, % p-$C_6H_4[CH_2P(O)Ph_2]_2$ |
|---|---|---|---|---|---|---|---|
| 4 | 6.0 | 16.0 | Acetonitrile, 100 | 6.4 | 30 | Stirred 1 hr. | 757.0 |
| 5 | 6.0 | 16.0 | 1,2-dimethoxyethane,100 | 6.4 | 30 | Refluxed 3¼ hrs. | 86.0 |
| 6 | 6.0 | 16.0 | 1,2-dimethoxyethane,150 | 14.0 | 30 | Stirred 27 min.; heated at 70° 10 min. | 92.5 |
| 7 | 6.0 | 16.0 | Tetrahydrofuran, 150 | 14.0 | 30 | Refluxed 1 hr. | 86.5 |
| 8 | 6.0 | 16.0 | Tetrahydrofuran, 150 | 14.0 | 30 | Stirred 1 hr. | 89.0 |
| 9 | 4.4 | 11.7 | Tetrahydrofuran, 110 | 10.3 | 22 | Refluxed 1 hr. | 91.0 |

EXAMPLE 10

A mixture of 120 g. of o-xylylenedichloride, 320 g. of chlorodiphenylphosphine, 3 liters of tetrahydrofuran and 280 g. of sodium hydroxide in 600 ml. of water was refluxed for 1 hour. The product precipitated and was removed by filtration. It was washed with cold tetrahydrofuran and with water to obtain a 92% yield of o-$C_6H_4[CH_2P(O)Ph_2]_2$.

EXAMPLE 11

A mixture of 100 g. of 2,4,6-tris(chloromethyl)mesitylene, 250 g. of chlorodiphenylphosphine, 2 liters of tetrahydrofuran and 225g. of sodium hydroxide in 500 ml. of water was refluxed for 1 hour after an initially very vigorous reaction had subsided. The precipitated product was removed by filtration and washed thoroughly with water to obtain a 70% yield of 2,4,6-tris(diphenylphosphorylmethyl)mesitylene.

EXAMPLE 12

A solution of 28 g. of sodium hydroxide (0.7 mole) in 60 ml. of water was added to a mixture of 55 g. of p-$BrCH_2C_6H_4Br$ (0.22 mole) and 45 g. of chlorodiphenylphosphine (0.20 mole) in 300 ml. of tetrahydrofuran. The mixture was refluxed for 1 hour, filtered, and the filter cake was washed with water until the washings were neutral. This left a crystalline white filter cake which was extracted with 1250 ml. of hot ethanol. Part of the filter cake (41.1 g) remained undissolved; part of the filter cake dissolved and 27 g. recrystallized from the filtered extracts on cooling. The undissolved and recrystallized materials were the same by infrared analysis (mp "undissolved": 241.5–242.2°; mp "recrystallized": 240.8–242.2°); together they comprised 68.1 g. (91%) of $(C_6H_5)_2P(O)CH_2C_6H_4Br$.

Anal. Calcd. for $C_{19}H_{16}BrOP$: C, 61.47; H, 4.34; Br, 21.52. Found: C, 61.36; H, 4.49; Br, 21.22.

EXAMPLES 13–19

These examples illustrate the use of a wide variety of solvents in the reaction of this invention.

A solution of 14 g. of sodium hydroxide in 30 ml. of water was added to a solution of 16 g. of chlorodiphenylphosphine and 6 g. of p-xylylenedichloride in 150 ml. of the designated solvent. The reaction was maintained at the designated temperature for 1 hour to give the designated yield of p-$C_6H_4[CH_2P(O)Ph_2]_2$. The data are given in Table III.

TABLE III

| Example | Solvent | Reaction Conditions | Yield, % |
|---|---|---|---|
| 13 | ethyl ether | reflux | 89.6 |
| 14 | benzene | reflux | 14.4 |
| 15 | water | reflux | 81.8 |
| 16 | o-dichlorobenzene | 100° C. | 23.6 |
| 17 | benzonitrile | 100° C. | 72.6 |
| 18 | dimethylformamide | 100° C. | 64.6 |
| 19 | pyridine | reflux | 8.1 |

EXAMPLE 20

A solution of 25 g. of $Ba(OH)_2.8H_2O$ in 45 ml. of hot water was added to a solution of 16 g. of chlorodiphenylphosphine and 6 g. of p-xylylenedichloride in 150 ml. of tetrahydrofuran. The mixture was heated at reflux temperature for one hour and then filtered hot. The filter cake was washed first with hot water and then with room temperature water until the washings were neutral. The filter cake was then dried to obtain 11.9 g. (68% yield) of p-$C_6H_4[CH_2P(O)Ph_2]_2$ which was identified by infrared absorption analysis.

We claim:
1. Method of preparing a phosphine oxide of the formula

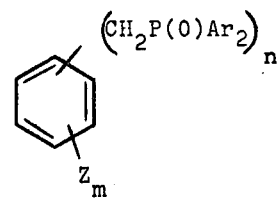

wherein Ar is a mono- or di-carbocyclic aromatic radical which may be substituted by up to 5 substituents selected from the group consisting of halogen and alkyls of 1 to 3 carbon atoms, Z is halogen or alkyl of 1 to 3 carbon atoms, $n$ is a whole number from 1 to 3, $m$ is a whole number from 0 to 5, and $n + m$ is a whole number from 1 to 6, which comprises reacting
1. a benzylic halide of the formula

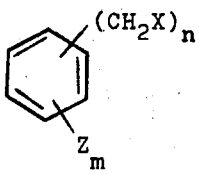

wherein X is chlorine, bromine or iodine; and Z, $n$ and $m$ are as specified above,
2. a diarylhalophosphine of the formula Ar$_2$PX' wherein Ar is as specified above, and X' is chlorine, bromine or iodine, and
3. a hydroxide selected from the group consisting of alkali metal hydroxides and alkaline earth metal hydroxides in the presence of a member selected from the group consisting of water, organic solvents, and mixtures thereof at a temperature of −50° to 250°C.

2. The method of claim 1 in which the benzylic halide is p-xylylene dichloride.

3. The method of claim 2 in which the diarylhalophosphine is chlorodiphenylphosphine.

4. The method of claim 3 in which the hydroxide is sodium hydroxide.

5. The method of claim 4 in which the reaction is carried out in the presence of an organic solvent which is capable of dissolving at least 1% by weight of water.

6. The method of claim 5 in which the solvent is 1,2-dimethoxyethane.

7. The method of claim 5 in which the solvent is tetrahydrofuran.

* * * * *